United States Patent [19]

Meybeck et al.

[11] Patent Number: 5,290,562
[45] Date of Patent: Mar. 1, 1994

[54] COMPOSITIONS AND METHODS EMPLOYING LIPOSOMES INCLUDING TYROSINE OR A TYROSINE DERIVATIVE

[75] Inventors: Alain Meybeck; Marc Dumas, both of Colombes, France

[73] Assignee: L V M H Recherche, Cedex, France

[21] Appl. No.: 789,397

[22] Filed: Nov. 7, 1991

Related U.S. Application Data

[63] Continuation of Ser. No. 302,235, Dec. 30, 1988, abandoned.

[30] Foreign Application Priority Data

Nov. 27, 1987 [FR] France .............................. 87 16524

[51] Int. Cl.$^5$ .............................................. A61K 9/127
[52] U.S. Cl. ...................................... 424/450; 424/63; 424/70; 424/401; 424/417; 424/420; 428/402.2; 514/880
[58] Field of Search ............... 424/450, 490, 455, 401, 424/417, 63, 59; 428/402.2, 70, 420; 514/880

[56] References Cited

U.S. PATENT DOCUMENTS

| | | |
|---|---|---|
| 3,899,288 | 8/1975 | Galerne . |
| 3,957,971 | 5/1976 | Oleniacz . |
| 3,993,436 | 11/1976 | Fujinuma . |
| 4,217,344 | 8/1980 | Vanlerberghe et al. . |
| 4,356,167 | 10/1982 | Kelly .................................. 424/450 |
| 4,419,343 | 12/1983 | Pauly . |
| 4,453,941 | 6/1984 | Jacobs ..................................... 8/424 |
| 4,508,703 | 4/1985 | Redziniak et al. . |
| 4,621,023 | 11/1986 | Redziniak et al. . |
| 4,652,441 | 3/1987 | Okada ................................. 424/490 |
| 4,731,210 | 3/1988 | Weder .................................. 264/4.3 |
| 4,762,471 | 9/1988 | Vanlerberghe et al. . |
| 4,783,332 | 11/1988 | Schreuder ............................ 424/59 |
| 4,830,858 | 5/1989 | Payne et al. ......................... 424/450 |
| 4,861,588 | 8/1989 | Neurath et al. ....................... 514/17 |
| 5,061,480 | 10/1991 | Marchese et al. ..................... 424/59 |

FOREIGN PATENT DOCUMENTS

| | | |
|---|---|---|
| 070048 | 1/1983 | European Pat. Off. . |
| 107559 | 5/1984 | European Pat. Off. . |
| 124077 | 11/1984 | European Pat. Off. . |
| 2932923 | 2/1981 | Fed. Rep. of Germany . |
| 2408387 | 6/1979 | France . |
| 2013609 | 8/1979 | United Kingdom . |
| 2176481 | 12/1986 | United Kingdom . |

OTHER PUBLICATIONS

Mezei et al. Life Sciences-26, p. 1473 (1980).
Johsi et al, "Involvement of Reactive Oxygen Species in the Oxidation of Tyrosine and Dopa to Melanin and in Skin Tanning", *Biochemical and Biophysical Research Communications*, vol. 142, No. 1, Jan. 15, 1987, pp. 265-274.
Christine Jaworsky, M.D. et al., "Efficacy of tan accelerators," Journal of the American Academy of Dermatology, vol. 16, No. 4, 1987, pp. 769-771.

*Primary Examiner*—Thurman K. Page
*Assistant Examiner*—G. S. Kishore
*Attorney, Agent, or Firm*—Lowe, Price, LeBlanc & Becker

[57] ABSTRACT

Compositions, for example cosmetic or pharmaceutical compositions, and methods of increasing melanin formation on the skin or scalp employ liposomes including between 0.001 and 10 weight percent, with respect to the total weight of the composition, of tyrosine or a tyrosine derivative selected from the group consisting of an alkali metal salt of L-tyrosine, an alkaline earth metal salt of L-tyrosine, methyl L-tyrosinate, ethyl L-tyrosinate, and stearyl L-tyrosinate.

17 Claims, 2 Drawing Sheets

COMPOSITIONS AND METHODS EMPLOYING LIPOSOMES INCLUDING TYROSINE OR A TYROSINE DERIVATIVE

This application is a continuation application of application Ser. No. 07/302,235, filed Dec. 30, 1988 now abandoned.

The subject of the present invention is a composition based on hydrated lipid lamellar phases or liposomes, containing tyrosine or a tyrosine derivative.

The invention finds application in particular in the cosmetic or pharmaceutical, and in particular dermatological, field for the development of compositions with pigmenting activity, capable of being used to accelerate the tanning of the skin, improve the complexion or retard the appearance of grey hair.

It is known that melanin pigments, responsable in particular for the black colour of the skin and hair, have a macromolecular structure, the predominant chemical units of which are formed from precursors, and in particular from tyrosine.

The article of PRAKASH C. JOSHI et al., Biochem. Biophys. Res. Commun. (1987) 142 (1) pages 265 to 274, recalls the biochemical mechanism for the conversion of tyrosine into melanin.

Thus, for a long time attempts have been made to develop cosmetic products based on tyrosine, destined in particular to promote the tanning of the skin and the pigmentation of hair.

However, tyrosine exhibits a certain hydrophilic character and penetrates with very great difficulty through the corneous layer to the level of the melanocytes. In consequence, research has been oriented towards products in which tyrosine is present in a modified form, both from the chemical and physical points of view.

It is in this way that the French patent FR-A-2 439 013 recommends the utilization of a salt complex of L-tyrosine with at least one aminoacid chosen from among arginine, ornithine, citrulline, lysine or hydroxylysine. The authors have shown that the salt complex just mentioned has an unexpected effect of activating tyrosinase naturally present in the epidermis.

Similarly, the document DE-2 932 923 discloses cosmetic compositions containing a tyrosine-arginine-urocanate complex, acting as promoter of melanin.

Cosmetic compositions have also been developed incorporating combinations of various compounds, among which tyrosine appears (FR-A-2 252 841 and U.S. Pat. No. 3,899,288).

Similarly, the document EP-124 077 discloses a composition destined to retard the appearance of grey hair. It is indicated there that the results obtained with this composition are better if a solution containing tyrosine is used prior to this composition.

Finally, the patent U.S. Pat. No. 4,453,941 describes the utilization of a specific derivative of tyrosine possessing a side chain capable of forming an indole nucleus, in combination with an aminoacid and an oxidant.

Thus for a long time there has existed a prejudice against the utilization of tyrosine alone in cosmetic compositions.

This prejudice was confirmed recently by an article of C. JAWORSKI et al., published in "Journal of the American Academy of Dermatology" 1987, vol. 16, 4, pages 769-771. The authors have not observed any significant effect of the compositions tested containing tyrosine on the acceleration of tanning of the skin. In addition, they point out that it is doubtful that tyrosine, a polar molecule, can pass through the corneum and thus penetrate to the basal layer of the epidermis where the melanocytes are located.

The use of hydrated lipid lamellar phases or liposomes in pharmaceutical compositions or cosmetic compositions, in which various active principles are incorporated (EP-B1-0 087 993) has also been known for a long time.

In opposition to the existing prejudice, the authors of the present invention have conducted research and demonstrated in a quite unexpected manner the fact that tyrosine or its derivatives, such as its salts or its esters, make it possible to obtain a measurable increase in the amount of melanin induced in the skin by ultraviolet rays when they are incorporated in a hydrated lipid lamellar phase or in liposomes. This discovery makes possible the development of cosmetic or pharmaceutical compositions incorporating tyrosine or one of its derivatives.

Thus it is possible to deduce from this in a way a potentiation effect of the activity of tyrosine and its derivatives as a result of their incorporation in hydrated lipid lamellar phases or in liposomes.

Thus, the present invention has the effect of resolving the new technical problem consisting of the provision of a novel formulation based on tyrosine or one of its derivatives, such as its salts or its esters, making it possible to potentiate their efficacy in order to permit their utilization in cosmetic or pharmaceutical, and in particular dermatological, compositions with pigmenting activity.

Thus, in accordance with a first feature, the present invention provides a composition based on hydrated lipid lamellar phases, or liposomes, preferably for the preparation of cosmetic or pharmaceutical compositions, characterized in that the said hydrated lipid lamellar phases or the said liposomes contain at least in part tyrosine or a derivative of tyrosine, such as a salt or an ester.

In the present description and the claims, the term "lipid" in the expression "lipid lamellar phase" covers all substances containing a so-called fatty carbon chain, usually more than 5 carbon atoms.

According to the invention, amphiphilic lipids are used, i.e. those constituted of molecules possessing a hydrophilic group, indiscriminately ionic or non-ionic, and a lipophilic group, such amphiphilic lipids being capable of forming lipid lamellar phases in the presence of an aqueous phase. In particular, among such lipids may be cited: the phospholipids, the phosphoaminolipids, the glycolipids, the polyoxyethylene fatty alcohols, the esters of polyols possibly of polyoxyethylene. Such substances are constituted for example by egg or soya lecithin, phosphatidylserine, sphingomyelin, a cerebroside or an oxyethylene derivative of polyglycerol stearate.

More particularly, tyrosine is L-tyrosine, and the tyrosine derivative mentioned earlier is chosen from among the group of compounds constituted by an alkaline L-tyrosinate or alkaline earth L-tyrosinate as for example sodium or calcium L-tyrosinate, methyl L-tyrosinate, ethyl L-tyrosinate, stearyl L-tyrosinate and a compound obtained from L-tyrosine and D (+) glucose.

As different reaction compounds can be prepared from D (+) glucose, all such compounds are included in the scope of the invention, taken individually or as a mixture. On the market, is found a mixture of these reaction compounds of D (+) glucose with L-tyrosine, in particular a mixture of esters, under the name "glucose tyrosinate".

The incorporation of tyrosine or its derivatives into the hydrated lipid lamellar phases or into liposomes can be carried out according to known procedures. These latter are chosen more particularly depending on the more or less lipophilic character or more or less hydrophilic character of the compound to be incorporated.

According to a preferred embodiment of the composition based on hydrated lipid lamellar phases or liposomes, a method of preparation described in the document EP-B1-0 087 993 is chosen, if necessary in combination with a method described in the document EP-B1-0 107 559.

Thus, it is for example possible to include tyrosine or the tyrosine derivative in hydrated lipid lamellar phases or liposomes in the following manner:

Step 1

An amphiphilic lipid, hydrogenated or not, such as soya lecithin, is dissolved in an organic solvent with a relatively low boiling point, for example lower than 100° C. at atmospheric pressure, such as dichloromethane or methanol. A hydrophobic lipid, such as a sterol, like cholesterol or β-sitosterol, and advantageously an anti-oxidant like α-tocopherol may also be dissolved.

The amount of hydrophobic lipid must usually not exceed 0.2 times the amount of amphiphilic lipid by weight.

Step 2

Tyrosine or the tyrosine derivative is then dispersed in the solution obtained. The relative proportions of lipid on the one hand and of tyrosine or the tyrosine derivative on the other are included between 8:2 and 9.9:0.1, by weight. Preferably, the mixture is stirred for 30 min at room temperature.

Step 3-A

The mixture obtained at the end of the second step is introduced into a rotary flask and evaporated by heating on a water-bath, under reduced pressure if required.

After evaporation, the lipid film deposited on the walls is taken up with shaking in water or in a suitable aqueous solution such as a buffer solution containing 0.8% of NaCl and 1.5% of $NaH_2PO_4$, called "phosphate buffer".

Preferably the amount of water or aqueous solution is at least equal to eight times the amount of lipid contained in the flask by weight.

A suspension of liposomes is thus obtained which can then be homogenized by appropriate means such as, for example, ultrasonics.

Step 3-B

According to a variant of the process for the preparation of the composition of the invention, the procedure described in the document EP-B1-0 087 993 is used, which includes the spraying of the mixture obtained at the end of the second step, followed by the dispersion of the lipid powder thus produced in a predetermined quantity of water or aqueous solution of substances to be encapsulated.

Hydrated lipid lamellar phases or a suspension of liposomes are obtained depending on whether one has chosen to disperse the lipid powder in a little or a great deal of the aqueous medium as is set out in the European document mentioned earlier.

The dispersion of lamellar phases or liposomes can then be homogenized, for example according to the procedure described in the document EP-B1-0 107 559.

Steps 3-C and 3-D

According to another variant, tyrosine or the tyrosine derivative is introduced directly into the aqueous medium in which the lipid phase will be dispersed.

For that, the organic solution obtained at the end of step 1 is evaporated, either (step 3-C) by means of a rotary flask as indicated in step 3-A, or (step 3-D) by means of a sprayer as indicated in step 3-B. The lipid film or lipid powder obtained, respectively, is then dispersed in an aqueous solution of tyrosine or tyrosine derivative.

Lipid lamellar phases or liposomes then form which contain at least in part the substances dissolved in the water.

It is then possible to homogenize by means of the procedures mentioned earlier.

Advantageously, the dispersions of hydrated lipid lamellar phases or the suspensions of liposomes obtained in steps 3 above, can be gelified for example by mixing them with a gel prepared separately, such as a gel of a vinyl polymer.

In accordance with a second feature, the present invention also relates to a cosmetic or pharmaceutical, and especially dermatological, composition with pigmenting activity, characterized in that it comprises a composition based on hydrated lipid lamellar phases or liposomes, such as previously defined.

Preferably, the proportion by weight of tyrosine or the tyrosine derivative is comprised between 0.001% and 10%, and preferably between 0.05% and 2% by weight, with respect to the total weight of the said cosmetic or pharmaceutical composition.

Other aims, properties and advantages of the invention will become more clearly apparent in the light of the explanatory description which follows, done with reference to several illustrative examples which will in no way limit the scope of the invention. In these examples, percentages are given by weight, unless indicated otherwise.

BRIEF DESCRIPTION OF THE DRAWING

The properties and advantages of the invention will become more fully apparent in view of the drawing in which.

EXAMPLE 1

Figure 1:
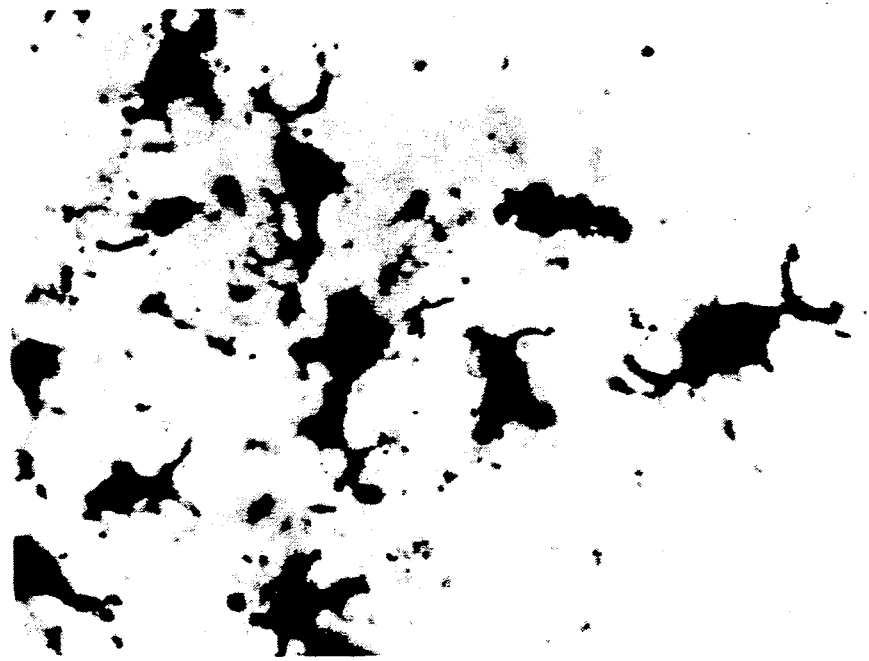
FIG. 1 is a photograph of an enlargement of a control epidermis.

Preparation of Hydrated Lipid Lamellar Phases Containing L-Tyrosine (Method A)

1.8 g of hydrogenated soya lecithin and 0.06 g of α-tocopherol are dissolved in 20 ml of dichloromethane, then 0.2 g of L-tyrosine are dispersed in this solution.

This mixture is evaporated under reduced pressure (about 200 mm of mercury) in a rotary flask heated at 45° C.

The lipid film obtained is taken up in 98 g of the solution called "phosphate buffer" mentioned earlier (pH equal to about 7.5) with gentle shaking for 3 h.

An aqueous suspension of liposomes is obtained after homogenization with ultrasonics (10 min, 100 W).

This suspension is then gelified by mixing it with an equal weight of a Carbopol 940 ® gel prepared in a standard manner at a concentration of 5% by weight.

About 200 g of a gelified composition based on liposomes is thus obtained, the tyrosine content of which is 0.1% by weight of this composition.

EXAMPLE 2

Preparation of Hydrated Lipid Lamellar Phases Containing L-Tyrosine (Method B)

36 g of soya lecithin, 0.5 g of $\alpha$-tocopherol and then 4 g of $\beta$-sitosterol are dissolved in 300 ml of dichloromethane. The solution thus obtained is sprayed at 65° C. as described in the patent EP-B1-0 087 993 so as to produce an intimate mixture of the two lipid constituents in the form of a fine powder.

Furthermore, 0.35 g of L-tyrosine are dissolved in 900 ml of the solution called "phosphate buffer" previously mentioned (pH equal to about 7,5). The sprayed lipid powder is then dispersed in the solution obtained by means of a magnetic stirrer for 3 h, then the dispersion is made up to 1000 g with distilled water, so as to obtain a suspension of liposomes of the following composition:

| Soya lecithin | 36 g |
|---|---|
| $\beta$-sitosterol | 4 g |
| $\alpha$-tocopherol | 0.5 g |
| L-tyrosine | 0.35 g |
| aqueous excipient to give | 1000 g |

This composition is homogenized by means of a homogenizer under pressure, for example according to the procedure described in patent EP-B1-0 107 559.

EXAMPLE 3

Preparation of Hydrated Lipid Lamellar Phases Containing the Methyl Ester of L-Tyrosine As in example 1, the procedure uses 1.8 g of hydrogenated soya lecithin, 0.2 g of the methyl ester of L-tyrosine and 0.06 g of $\alpha$-tocopherol which are dissolved in 80 ml of methanol. This solution is evaporated under reduced pressure (about 200 mm of mercury) in a rotary flask at about 56° C. The lipid film is taken up by 98 g of the solution called "phosphate buffer" mentioned earlier (pH equal to about 7.5). After homogenization with ultrasonics for 10 mn at 100 W and with magnetic stirring for 3 hours, a suspension of liposomes is obtained containing methyl L-tyrosinate which can be gelified with a Carbopol 940 ® gel. The mean size of the liposomes, measured with a Nano-Sizer ®, is 85.2 nm.

EXAMPLE 4

Preparation of Hydrated Lipid Lamellar Phases Containing "Glucose Tyrosinate"

1.0 g of a commercial solution of "glucose tyrosinate" (20% aqueous-alcoholic solution) is diluted in 15 ml of methanol. 25 ml of a solution of 3.8 g of soya lecithin, 0.2 g of $\beta$-sitosterol and 0.1 g of $\alpha$-tocopherol in dichloromethane are added to it.

The solution obtained is sprayed at 75° C. as described in the European patent EP-B1-0 087 993 so as to produce 5 g of powder of the lipid mixture. The lipid powder is dispersed in 47.5 g of demineralized water, with moderate stirring for 2 h. A suspension of lipid lamellar phases is obtained which is homogenized by ultrasonics for 10 min at 100 W in an icebath.

The 50 g of homogenized suspension of liposomes obtained are then gelified by the addition of 50 g of a 1% Carbopol 940 ® gel.

The size of the liposomes, measured with a Nano-Sizer ®, is 145.5±0.8 nm.

EXAMPLE 5

Demonstration of the Pigmenting Activity of the Tyrosine Included in Liposomes

In order to study the pigmenting activity of these compositions according to the invention, an attempt was made to demonstrate the increase of melanogenesis in the mouse in vivo.

This type of experiment was performed on $C_3H$ mice by daily applications of the product to be tested, followed by irradiation.

3 Groups of 6 mice were used. The first group (referred to hereafter as "non-irradiated control") was subjected neither to administration of the product nor to irradiation with U.V.

The second group (referred to hereafter as "irradiated control") was not subjected to administration of the product but was subject to daily irradiation with U.V. 5 days per week for three weeks.

Finally, the third group was subjected to a daily application of the product to be tested followed by irradiation with U.V., under the same conditions as the second group.

In order to carry out this experiment, the product obtained in the form of a gel in example 2 was applied to the tail of the mice for 5 days per week for 3 weeks. The product is applied in a quantity of about 0.2 ml (varying according to the length of the tail) about ¼ of an hour before irradiation.

At the time of each irradiation, the mice of groups 2 and 3 have their tail exposed for 150 s at a distance of 26.5 cm from a 2500 W xenon OSRAM ® lamp equipped with a water filter in order to suppress long wavelengths and a WG 320 filter in order to filter the U.V.C. The electrical intensity was adjusted to 54 A, and the powers of irradiation of U.V.B. and U.V.A. are 3 mW and 22 mW, respectively.

The mice of the three groups are then sacrificed, two fragments of tail skin are taken from each of them by biopsy which are immersed in a 2N solution of sodium bromide for 3 h at ambiant temperature in order to separate the epidermis.

Pieces of epidermis are removed with the aid of forceps, then they are rinsed for 1 min with distilled water, dried and weighed.

Thus, for each mouse, it is possible to measure the melanin formed with the first fragment and carry out a microscopic observation on the second fragment.

A-Measurement of the Melanin Formed

The dried and weighed fragments of epidermis are subjected to digestion with trypsin at 37° C. for 48 h.

A filtration is then carried out as is a centrifugation at 3000 rev/min for 30 min.

The melanin pellet of each mouse is recovered and suspended in a quantity of distilled water necessary for the measurement of the optical density.

The optical density is measured in a standard manner at 400 nm.

The values recorded are then related to 100 mg of weight of sampled epidermis and a mean value of the optical density is determined which is the only one to be taken into consideration. The results of these measurements are given in table I below.

This table contains the measurement of the optical density for each mouse as well as the mean of these densities for each group (values underlined).

It is very clearly apparent that the amount of melanin formed, linked to the value of the optical density, is much larger for the mice of the third group which received an application of the composition of example 2, namely a composition based on liposomes containing tyrosine, before each irradation.

B-Microscopic Observation of the Fragments of Epidermis

By means of these observations, an attempt is made to characterize the appearance of the epidermis in the three groups of mice by visualizing the melanocytes in particular.

The visualization of the melanocytes is carried out according to the method referred to as the DOPA reaction, according to the technique described by Renato J. STARICCO and Hermann PINKUS (Journal of Investigative Dermatology, 1956 pages 33-45).

The fragments of epidermis taken and treated as indicated above are incubated in a buffered solution of 0.1% dl-dopa at 37° C. for 1 h. This incubation medium is then changed and incubation is continued for 6 to 7 h.

The epidermises are then fixed with 10% formol overnight, then dehydrated with absolute alcohol, lightened with toluene and finally mounted between a glass slide and a coverslip, in order to be photographed at an enlargement ×475.

In the drawing, three photographs are shown corresponding to each of the groups with the same numbering system and selected as a function of their representativeness.

FIG. 1 (control): the melanocytes are quite small, their dendrites are few in number and short. The background is transparent.

Figure 2:
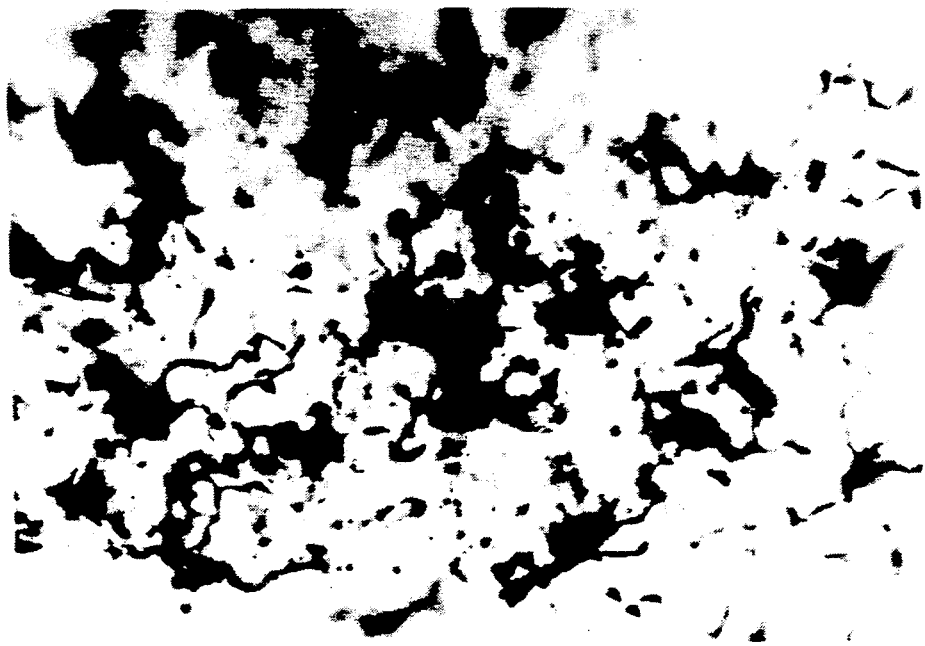
FIG. 2 is a photograph of an enlargement of a control epidermis subjected to UV radiation.

FIG. 2 (control+U.V.): the melanocytes exhibit a larger number of dendrites than in FIG. 1, some of them are much longer and the background is slightly grey.

Figure 3:
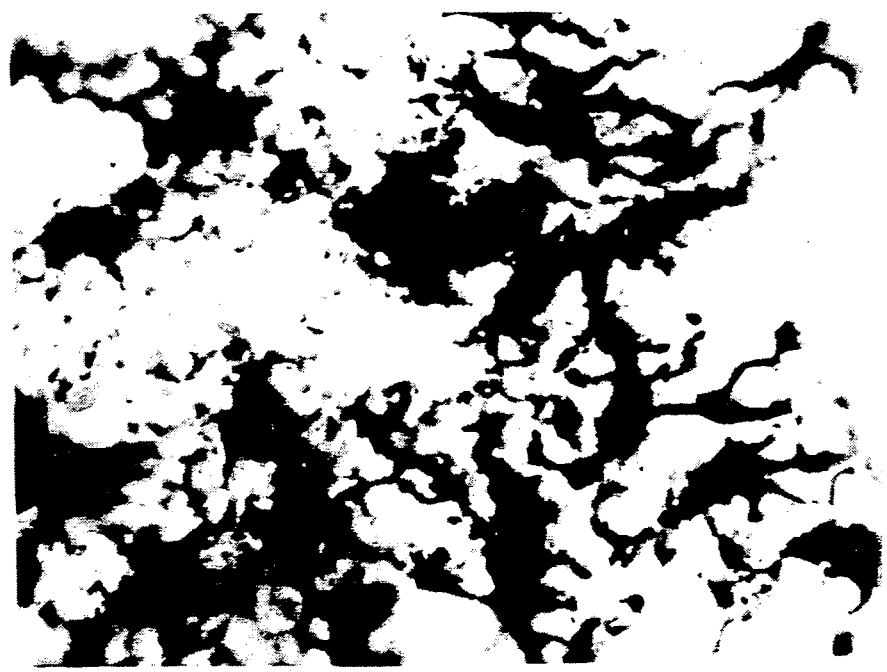
FIG. 3 is a photograph of an enlargement of an epidermis treated with the composition according to the present invention and subjected to UV radiation.

FIG. 3 (composition ex. 2+U.V.): the melanocytes are much bigger than in the previous two photos, the dendrites are at the same time numerous, longer and above all thicker. The background is grey, sprinkled with dark grains constituted by the released melanin.

Thus, it is obvious that the composition based on liposomes containing tyrosine has brought about a very marked increase in the activity of the melanocytes in the mice of group 3.

This in vivo experiment in the mouse clearly demonstrates the stimulating activity of the compositions according to the invention on melanogenesis as well as their value for the preparation of cosmetic or dermatological compositions with pigmenting activity.

TABLE I

| CONTROL | CONTROL + U.V. | Composition example 2 + U.V. |
|---|---|---|
| 275 | 335 | 494 |
| 221 | 682 | 826 |
| 381 | 520 | 955 |
| 224 | 624 | 433 |
| 293 | 588 | 545 |
| — | 492 | 423 |
| 278,8 | 540,1 | 612,6 |

EXAMPLE 6

Cosmetic Composition in Gel Form

The composition according to example 1 can be utilized as it is as a cosmetic composition in the form of a gel.

This gel is applied daily to prepare the skin for the sun. This treatment is preferably practiced eight days before any exposure to the sun.

EXAMPLE 7

Sun Cosmetic Composition

A gelified suspension of liposomes according to example 4 is prepared with the following composition:

| | |
|---|---|
| Soya lecithin | 3.8 g |
| β-sitosterol | 0.2 g |
| α-tocopherol | 0.1 g |
| "glucose tyrosinate" | 1 g |
| gelified aqueous excipients to give | 100 g |

This suspension is mixed with an equal volume of an oil-in-water emulsion prepared separately in a standard manner and containing an U.V. filter such as Parsol MCX ® at a concentration of 3%.

The composition obtained can be used as a sun tan milk.

EXAMPLE 8

Cosmetic Composition in the Form of a Lotion

A gelified suspension of liposomes according to the procedure described in example 1 is prepared by using, however, a Carbopol 940 ® gel two times less concentrated and a composition defined as follows:

| | |
|---|---|
| hydrogenated soya lecithin | 9 g |
| L-tyrosine | 1 g |
| gelified aqueous excipients + perfumes to give | 100 g |

This lotion, applied morning and evening to the scalp, retards the appearance of grey hair.

EXAMPLE 9

Cream for Improving the Complexion

| | |
|---|---|
| Soya lecithin | 2 g |
| α-tocopherol | 0.06 g |
| L-tyrosine | 0.2 g |
| excipients for oil-in-water emulsion to give | 100 g |

A suspension of liposomes according to example 1, on the one hand, and an oil-in-water emulsion, on the other are prepared separately.

These two preparations are then mixed in the ratio of one volume of suspension of liposomes for three volumes of emulsion.

The cream obtained applied daily to the face, preferably in the morning, restores the complexion.

We claim:

1. A composition comprising liposomes including between 0.001 and 10 weight percent, with respect to the total weight of the composition, of tyrosine or a tyrosine derivative selected from the group consisting of an alkali metal salt of L-tyrosine, an alkaline earth metal salt of L-tyrosine, methyl L-tyrosinate, ethyl L-tyrosinate, and stearyl L-tyrosinate.

2. A composition according to claim 1, further including a sterol.

3. A composition according to claim 1, further including β-sitosterol.

4. A composition according to claim 1, wherein the tyrosine is L-tyrosine.

5. A composition according to claim 1, wherein the tyrosine or tyrosine derivative is included in an amount between 0.05 and 2 weight percent with respect to the total weight of the composition.

6. A cosmetic or pharmaceutical composition, comprising liposomes including tyrosine or a tyrosine derivative selected from the group consisting of an alkali metal salt of L-tyrosine, an alkaline earth metal salt of L-tyrosine, methyl L-tyrosinate, ethyl L-tyrosinate, and stearyl L-tyrosinate, the tyrosine or tyrosine derivative being included in the composition in an amount sufficient to stimulate melanin formation.

7. A composition according to claim 6, further including a sterol.

8. A composition according to claim 6, further including β-sitosterol.

9. A composition according to claim 6, wherein the tyrosine is L-tyrosine.

10. A composition according to claim 6, wherein the tyrosine or tyrosine derivative is included in an amount between 0.05 and 2 weight percent with respect to the total weight of the composition.

11. A cosmetic or pharmaceutical composition, comprising liposomes including between 0.001 and 10 weight percent, with respect to the total weight of the composition, of tyrosine or a tyrosine derivative selected from the group consisting of an alkali metal salt of L-tyrosine, an alkaline earth metal salt of L-tyrosine, methyl L-tyrosinate, ethyl L-tyrosinate, and stearyl L-tyrosinate.

12. A method of increasing melanin formation on the skin or scalp, comprising applying on the skin or scalp a composition comprising liposomes including tyrosine or a tyrosine derivative selected from the group consisting of an alkali metal salt of L-tyrosine, an alkaline earth metal salt of L-tyrosine, methyl L-tyrosinate, ethyl L-tyrosinate, and stearyl L-tyrosinate, the tyrosine or tyrosine derivative being included in the composition in an amount sufficient to stimulate melanin formation.

13. A method as defined by claim 12, wherein the tyrosine or tyrosine derivative is included in an amount between 0.05 and 2 weight percent, with respect to the total weight of the composition.

14. A method as defined by claim 12, wherein the composition further includes a sterol.

15. A method according to claim 12, wherein the composition further includes β-sitosterol.

16. A method according to claim 12, wherein the composition comprises L-tyrosine.

17. A method of increasing melanin formation on the skin or scalp, comprising applying on the skin or scalp a composition comprising liposomes including between 0.001 and 10 weight percent, with respect to the total weight of the composition, of tyrosine or a tyrosine derivative selected from the group consisting of an alkali metal salt of L-tyrosine, an alkaline earth metal salt of L-tyrosine, methyl L-tyrosinate, ethyl L-tyrosinate, and stearyl L-tyrosinate.

* * * * *